United States Patent [19]

Shaw

[11] 4,111,191

[45] Sep. 5, 1978

[54] APPARATUS AND METHOD FOR EXAMINING BLOOD VESSELS OF INTEREST BY TRACKING POSITION WITH RESPECT TO TIME OF PARTICLES INTRODUCED THEREIN

[76] Inventor: Robert F. Shaw, 50 St. Germain Ave., San Francisco, Calif. 94114

[21] Appl. No.: 487,425

[22] Filed: Jul. 10, 1974

Related U.S. Application Data

[63] Continuation of Ser. No. 249,161, May 1, 1972, abandoned.

[51] Int. Cl.$^2$ ............................................. A61B 5/02
[52] U.S. Cl. ............................... 128/2.05 F; 128/2 A
[58] Field of Search ................. 128/2 A, 2 R, 2.05 F, 128/2.05 R, 2.1 R; 250/260, 272, 273, 308

[56] References Cited

U.S. PATENT DOCUMENTS

| | | | |
|---|---|---|---|
| 3,221,731 | 12/1965 | Annis et al. | 128/2.1 R |
| 3,344,275 | 9/1967 | Marchal et al. | 128/2 A |
| 3,622,784 | 11/1971 | Del Guercio | 128/2.1 R |
| 3,640,271 | 2/1972 | Horton | 128/2.05 F |
| 3,689,393 | 9/1972 | Davis | 128/2.05 F |
| 3,736,918 | 6/1973 | Mutschelknauss et al. | 128/2.05 F |
| 3,769,966 | 11/1973 | Youdin et al. | 128/2 A |
| 3,777,740 | 12/1973 | Hokanson | 128/2.05 Z |

Primary Examiner—William E. Kamm
Attorney, Agent, or Firm—A. C. Smith

[57] ABSTRACT

The extent, location, and severity of stenotic atherosclerotic lesions in the coronary arteries are determined by intravenous injection into the circulating blood of a number of small, discrete positron-emitting particles and by tracking the particles in three dimensions in the region of the heart using suitable gamma detectors disposed external to the patient's chest. The resolution and counting rates of the gamma detectors permit the sequence of positions of each particle to be recorded as a function of time as each particle flows through a coronary vessel. Data analysis of these recordings of particle position provide information about the velocity of blood flow through the course of each coronary artery. This velocity information is used to determine the extent, severity, and location of stenotic lesions of the coronary arteries.

51 Claims, 6 Drawing Figures

APPARATUS AND METHOD FOR EXAMINING BLOOD VESSELS OF INTEREST BY TRACKING POSITION WITH RESPECT TO TIME OF PARTICLES INTRODUCED THEREIN

CROSS REFERENCE TO RELATED APPLICATION

This is a continuation of application Ser. No. 249,161, filed May 1, 1972 and now abandoned.

BACKGROUND OF THE INVENTION

Coronary heart disease (CHD) is the leading cause of death in the United States and the western world. Coronary heart disease accounts for almost two-thirds of male deaths during that period of life (30–64 years) when responsibilities to family and society are the greatest. Approximately one-third of individuals dying of coronary heart disease succumb immediately after coronary occlusions; one-third die within a few hours; and only one-third receive the benefits of hospital therapy. Of all individuals sustaining their first myocardial infarction, more than half have had neither preceding signs nor symptoms of coronary heart disease.

During the past two years, coronary vein-graft by-pass surgery has been demonstrated to be an effective therapeutic modality of wide applicability. Because over 70% of all coronary artery stenoses occur in the first 4 cm. of the coronary arterial tree, a high percentage of all coronary lesions can be surgically by-passed with a low mortality and high patency rate.

Extensive epidemiological studies have delineated those factors (hypercholesterolemia, hypertension, obesity, and heavy smoking) that are statistically correlated with an increased incidence of coronary heart disease. But while a patient may be well advised to remove himself from the higher risk group by appropriately altering his manner of living, these indices cannot for any given patient furnish information concerning the existence of coronary stenotic lesions nor furnish a basis for clinical decisions regarding therapeutic intervention.

Electrocardiographic stress testing has been suggested as a means for screening individuals for significant coronary lesions. However, in a large prospective study in which objects underwent repeated testing, the sensitivity of this test was found to be too low (only 30%) to be adequate.

At present, coronary arteriography yields more useful information about the state of the coronary arteries than any other technique. However, in a large cooperative study, the incidence of major complications was 2% and the mortality rate was 0.23%. In addition to the dangers, the procedure is painful, expensive, and time-consuming. For these reasons, coronary angiography is not performed upon asymptomatic individuals and is not suitable for screening large populations.

The above considerations highlight the importance of the subject invention which furnishes the capability for detecting the extent, location and severity of coronary stenotic lesions by means of apparatus operating external to the body, thereby identifying, by means suitable for screening large populations, candidates for remedial coronary surgery and other therapeutic measures.

SUMMARY OF THE INVENTION

In accordance with the present invention, stenotic atherosclerotic lesions of the coronary arteries are detected by injecting a number of positron-emitting particles into the circulating blood of a subject to determine the velocity of blood flow through his coronary vessels.

Because of the high peripheral resistance of the myocardial vascular bed and the considerable range of autoregulatory resistance changes available to the coronary circulation, coronary stenoses of 80%–90% are required to diminish the volume of coronary blood flow. This propensity of volumetric coronary blood flow to remain normal even in the presence of severe stenoses is responsible for the late occurrence or absence of anginal symptoms and diagnostic electrocardiogram patterns, even in the presence of coronary stenoses, and explains why measurement of volumetric blood flow furnishes poor sensitivity in detecting coronary disease.

However, this propensity of volumetric blood flow to remain normal even in the presence of severe stenosis furnishes a distinctive characteristic that blood flowing through a stenotic arterial segment must have high velocity. In fact, to maintain the constant volumetric flow rate, the average fluid velocity within a stenotic segment of artery must change in strict inverse proportionality to the change in cross-sectional areas from normal to stenotic blood vessel. As coronary stenosis becomes more severe, the increments in blood flow velocity become progressively greater.

Discrete positron-emitting radioactive particles of sufficiently small size to pass through capillary beds are injected intravenously and become randomly distributed in the circulating blood volume. The particles are tracked in three dimensions whenever they appear in the region of the heart by means of high resolution high-speed gamma detectors that surround the chest. These recordings of particle position as a function of time are analyzed and whenever a particle follows a flow path indicating that it is passing through a coronary artery, the velocity of blood as it flows through the artery is measured by timing the transit of the particle. From the accumulated data of multiple particle transits through the coronary circulation, a three-dimensional representation of the lumen of the coronary arterial system is constructed.

DESCRIPTION OF THE PREFERRED EMBODIMENT

Figure 1:
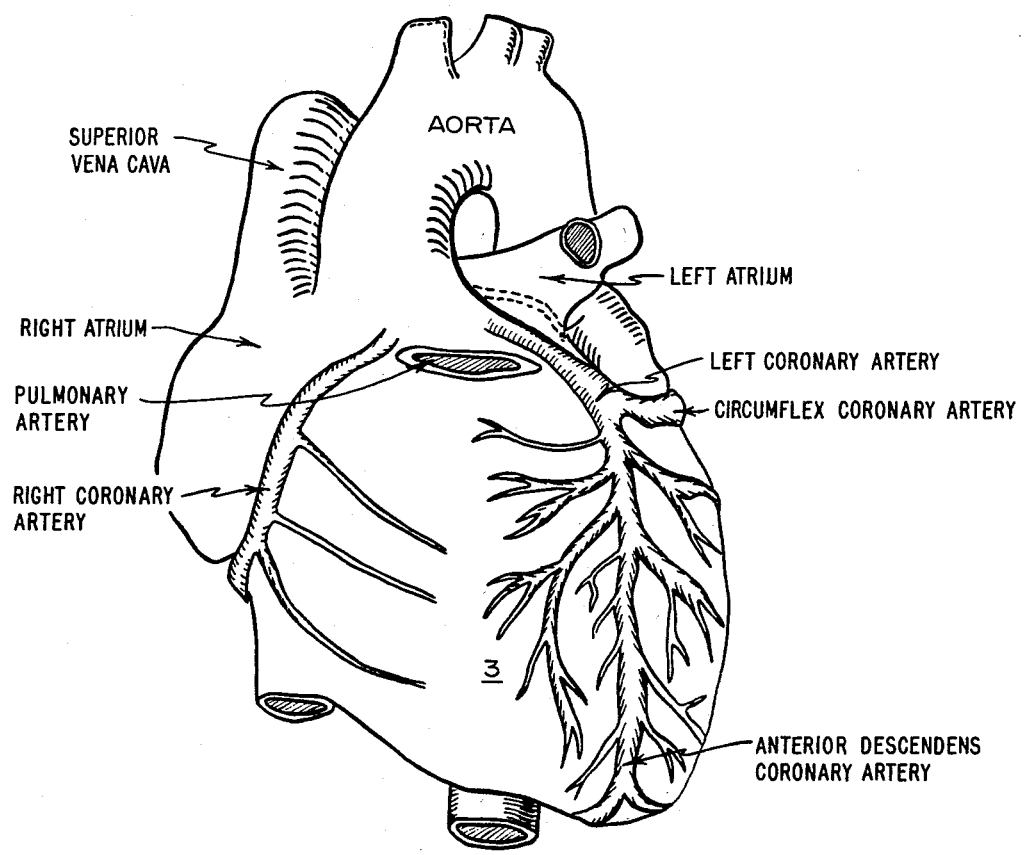
FIG. 1 is a pictorial view of a human heart showing the principal coronary arteries.

The main coronary arteries are three in number. These three vessels branch somewhat irregularly to form an average of ten secondary vessels, as shown in FIG. 1. Arteriosclerotic lesions are limited to the epicardial segments of the coronary vessels and rarely extend beyond the most proximal portions of the secondary vessels. The highest concentration of arteriosclerotic lesions is within the first 2 to 3 cm. of the left anterior descendens artery 3, but the lesions are otherwise rather randomly distributed in the proximal primary and secondary arteries. Seventy percent of all arteriosclerotic coronary lesions are found within the proximal 4 cm. of the main coronary arteries.

The average velocity of blood flow through the epicardial coronary blood vessels is of the order of 30 cm/sec. A 50% stenosis is generally considered to be significant. To be useful, the system should be capable of discriminating between normal vessels and 50% stenotic lesions and should be capable of assessing additional significant decrements in the patent cross sections of these vessels.

Typical blood flow velocities through stenoses of varying degrees are as follows:

| Degree of Stenosis | Average Velocity |
| --- | --- |
| 0% | 30 cm/sec |
| 50% | 60 cm/sec |
| 60% | 75 cm/sec |
| 70% | 100 cm/sec |
| 80% | 150 cm/sec |
| 90% | 300 cm/sec |

Since nominal resting coronary flow velocity is about 30 cm/sec, ideally the system should be able to differentiate a flow velocity of 60–75 cm/sec from 30 cm/sec in order to detect significant lesions and discriminate between velocities of 75, 100, 150, and 300 cm/sec in order to follow additional 10% increments in stenoses.

For a number of years, positron-emitting isotopes have been used to carry out tracer studies. A position from a typical emitting radionuclide will travel some millimeters in blood or tissue before coming to rest. It will then be captured by an electron in the local tissue and both particles will be annihilated producing two gamma rays, each of 511 KeV moving in almost exactly opposite directions. If both gamma rays can be detected at some distance with good spatial resolution, then a straight line joining the points at which the gamma rays were detected must pass through their mutual point of origin and within a few millimeters of the positron-emitting source. If a number of gamma pairs are detected from a single stationary source and several (in principle, two) such lines are drawn, the lines will intersect at one point in space and define the position of the positron-emitting source.

In the conventional applications of positron technology which have been made to date, rather poor resolution has been all that was required. A radioactive tracer is injected and then concentrates to some extent in an organ of interest. Typically, conventional detectors have spatial resolutions of the order of a centimeter. Since the organ being examined is normally stationary, any additional resolution is obtained by observing a statistically large number of counts.

In accordance with the preferred embodiment, the present invention tracks a number of discrete moving positron-emitting sources present in the circulating blood. The system not only locates the position of the sources in three dimensions, but also locates them again and again at very short time intervals. The requirement as to how often a particle source must be located is determined from the following considerations.

As noted above, 30 cm/sec is about the nominal velocity of blood flow through a coronary artery for a subject at rest. Blood flow through a diseased arterial segment which is 80% stenotic will have a velocity five times this nominal value (150 cm/sec). Blood flowing through a segment of a blood vessel with a severe 90% stenosis will have a velocity of the order of 300 cm/sec. In order to measure a 90% stenosis that is 1 cm long, a particle moving through the stenosis should be detected at least a few times. At 300 cm/sec, only three milliseconds are required to pass through a 1 cm length of vessel. If three determinations of position are desirable during this interval, a half-dozen coincident pairs of gamma rays must be detected during the three milliseconds and a minimum detection rate of 2,000 gamma pairs per second is indicated.

The detector of the present invention subtends about two-thirds of the total solid angle surrounding the heart. Each gamma ray has a 50% probability of leaving the body undeflected. There is thus a $(0.5)^2 = 0.25$ probability that both members of a gamma pair will emerge from the body undeflected.

If the detecting element has a 20% efficiency for detecting a gamma ray incident upon it, then there is a $(0.20)^2 = 0.04$ probability of detecting both members of a coincident pair. Multiplying these numbers together furnishes the over-all probability that a positron annihilation will produce a detected pair of $$P = 0.67 \times 0.25 \times 0.04 = 0.0067$$

Thus, it takes 150 annihilations on the average to produce one detected pair. For 2,000 detected gamma pairs per second, each source must emit $2,000 \times 150 = 3 \times 10^5$ positrons per second. $3.7 \times 10^5$ positrons per second correspond to a 10 microcurie source, so individual source intensities on the order of 10 microcuries are indicated.

Sources of this or many times greater intensity are routinely available, but the particles used in this application must be sufficiently small to pass through capillary beds, if they are to be injected by simple venipunctures and find their way to the coronary arteries. Fortunately, there exist a considerable number of positron emitters (such as $Gallium_{68}$) which have half-lives of sufficiently short duration so that a small number of atoms produce a high decay rate. For example, $Gallium_{68}$ has a half-life of only 68 minutes and can be readily, conveniently, and inexpensively "milked" from $Germanium_{68}$, an isotope with about 270 days half-life. A pure Gallium source of one cubic micron volume has an intensity of 230 microcuries. While pure $Gallium_{68}$ is unsuitable because it is a liquid at body temperature, the large carrier-to-active material ratios for particles having a short dimension less than 6–8 microns suggest that $Gallium_{68}$ either compounded or absorbed in carrier particles would provide a suitable source.

As noted above, there are three main coronary arteries which branch into an average of ten secondary branches. If, for statistical purposes, it is desired that three velocity measurements be made through each of the ten secondary branches, then a total $3 \times 10 = 30$ particle transits through the coronary system would be required. This would furnish approximately 10 transits through each of the proximal principal coronary arteries where most of the atheromatous lesions are located.

Since coronary blood flow approximates only 5% of the cardiac output at rest, a given particle has only a 0.05 probability of entering the coronary circulation after a single pass through the heart. Thus, 20 circulations through the heart times 30 particle transits through the coronary system, or a total of 600 particle transits through the circulation would furnish the redundancy of coronary blood flow velocity measurements outlined above.

Since the mean circulation time is 1 minute or less, a single particle tracked in the circulation for 600 minutes would be suitable for the outlined redundancy, if its half-life were sufficiently long and if it continued to circulate for the 10-hour period. Of course, 10 hours is an inconveniently long duration for a diagnostic measurement. Forty particles circulating for 15 minutes would be much more convenient and would furnish a comparable 600 particle transit through the circulatory system.

The number of particles required to attain 600 particle transits through the circulation is influenced by the possibility that the positron-emitting particles may be removed from the circulation by the Kupfer cells of the liver. The propensity of the liver to extract particles is a function of their size and surface characteristics, of the state of the reticuloendothelial system as influenced by pre-treatment and otherwise, and a function of other variables.

Liver blood flow is on the order of 20%-25% of cardiac output at rest. If particles are extracted by the liver with 100% efficiency, a total of 160 particles would have to be administered and the examination conducted for a 15-minute period in order to furnish the desired 600 circulatory transits under these circumstances. A reasonable program of particle administration might begin with an initial intravenous injection of 50 particles, with 12 particles injected at the end of each of nine subsequent 1-minute periods. Alternatively, if particles are extracted from the liver with less than 100% efficiency, the number of particles required for a 15-minute examination would fall between 160 and 40.

The number of particles used for an examination is important in two regards: the radiation exposure of the patient and the complexity of the data processing required. If liver extraction is 100% efficient, the total administered dose is 160 particles × 10 microcuries per particle = 1.6 millicuries, which compares favorably with the 2 millicurie Gallium$_{68}$ dose currently administered for bone scanning. Radiation to the liver for this worst case is 3 rads, which compares favorably with the liver dose of 6 rads which results from conventional liver scans using Gold$_{198}$. However, if the circulating particles are not picked up by the liver during the 15-minute examination time, only 40 particles constituting 0.4 millicurie need be administered. Since Gallium$_{68}$ has a radioactive half-life of only 68 minutes, if the circulating particles are not extracted by the liver over a period of a few hours, radiation of the liver is essentially zero and radiation to the rest of the body is so widely dispersed as to be negligible.

The complexity of data processing is significantly influenced by the number of particles that must be simultaneously detected in the field of view which encompasses the heart. The coincidence circuit 9 and gates 11, 13, shown in FIG. 2, connected to the gamma detectors 7, 8, of the type shown in FIG. 3, constitute a preprocessing circuit that accepts only those gamma rays which occur as synchronous pairs and which emerge from the general region of the heart. The field of view of detectors 7 and 8 thus situated contains only 5%-7% of the total blood volume. Even if the efficiency of hepatic extraction is 100%, the total number of particles in the entire circulating blood volume at any one time need be no more than 50 to obtain the highly redundant number of measurements described above. Under these extreme circumstances, no more than 3-4 particles need be in the field of view at any one time, a very acceptable number for uncomplicated data processing.

Figure 2:
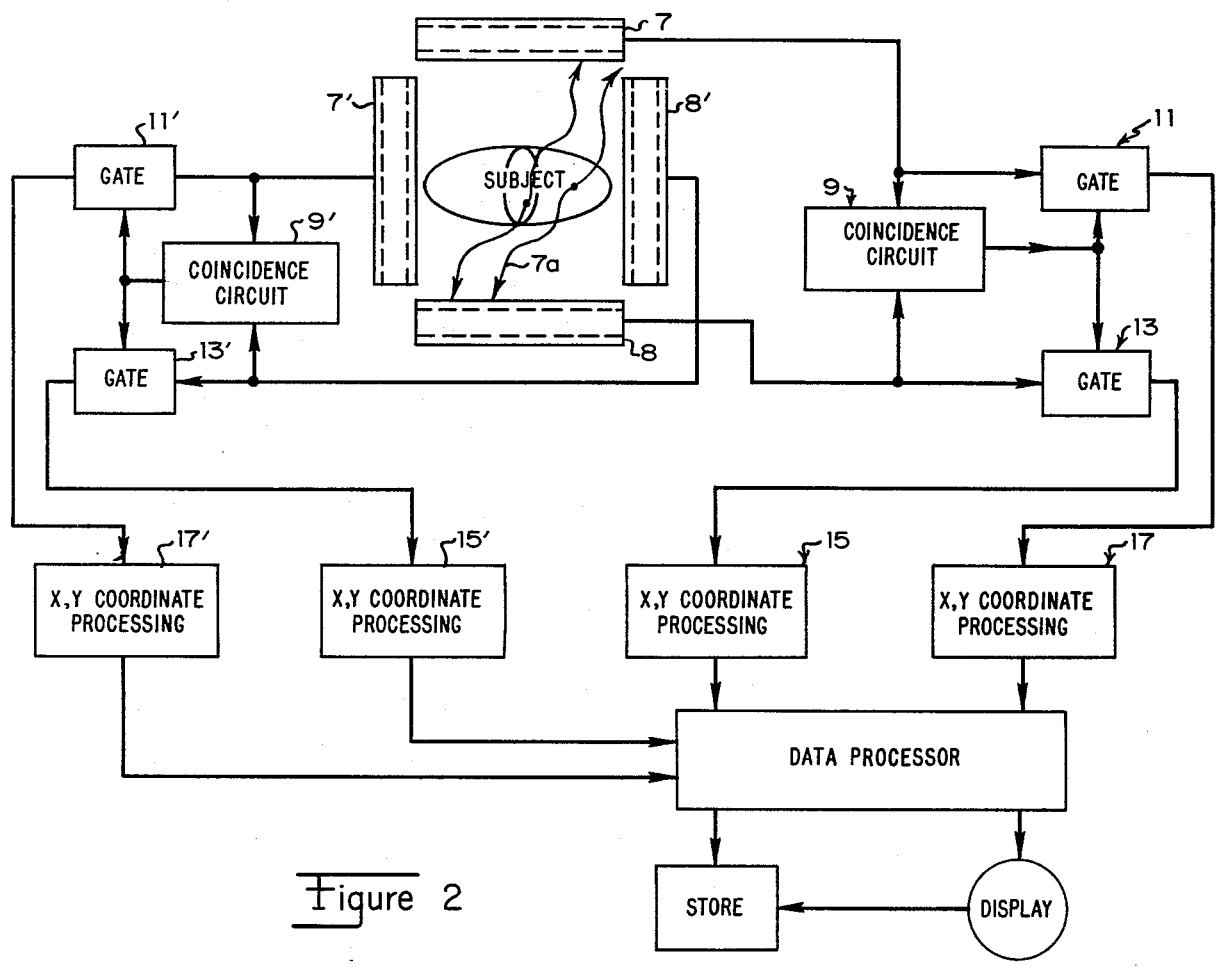
FIG. 2 is a schematic diagram of the apparatus of the present invention.
Figure 3:
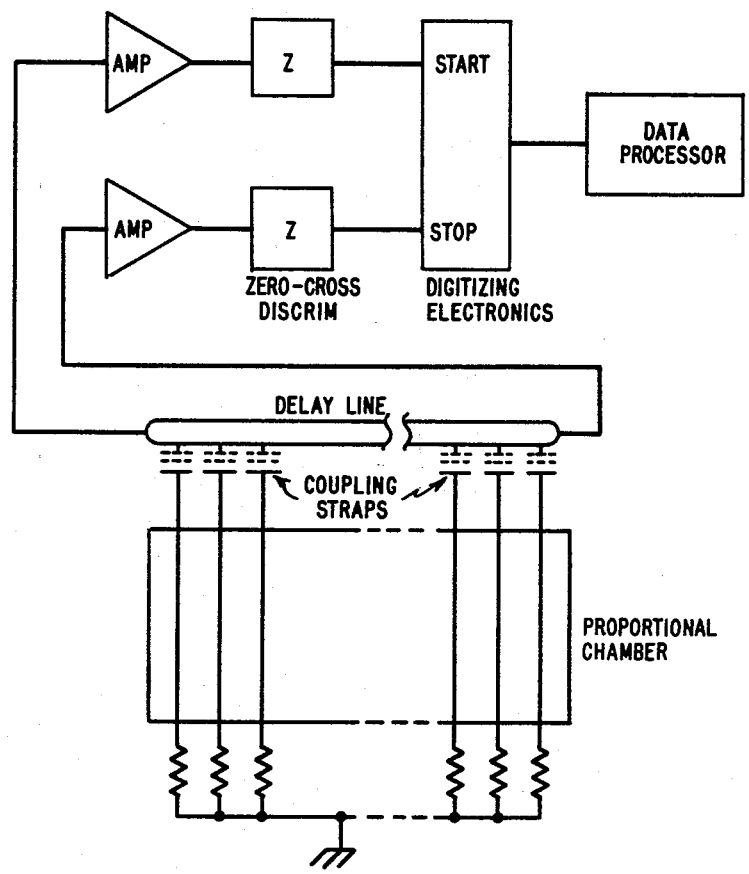
FIG. 3 is a schematic diagram of a multi-wire proportional chamber which may be used as the detectors of FIG. 1.

The detectors 7 and 8 consist of two or more pairs of detecting modules for example, of the type shown in FIG. 3 which surround the thorax, as shown in FIG. 2, and locate the arriving gamma rays to an accuracy of about a millimeter. This information, which exists in the form of electrical pulses, is stored, say on tape or disc, depending on the rate of events, for subsequent computer processing. As noted, only gamma rays that arrive synchronously on opposing detectors 7 and 8 and only synchronous pairs that could have originated in the region of the heart are accepted for recording. Thus, gamma rays 7a that arrive synchronously from a region beyond the heart may be conveniently rejected as irrelevant data.

Figure 5:
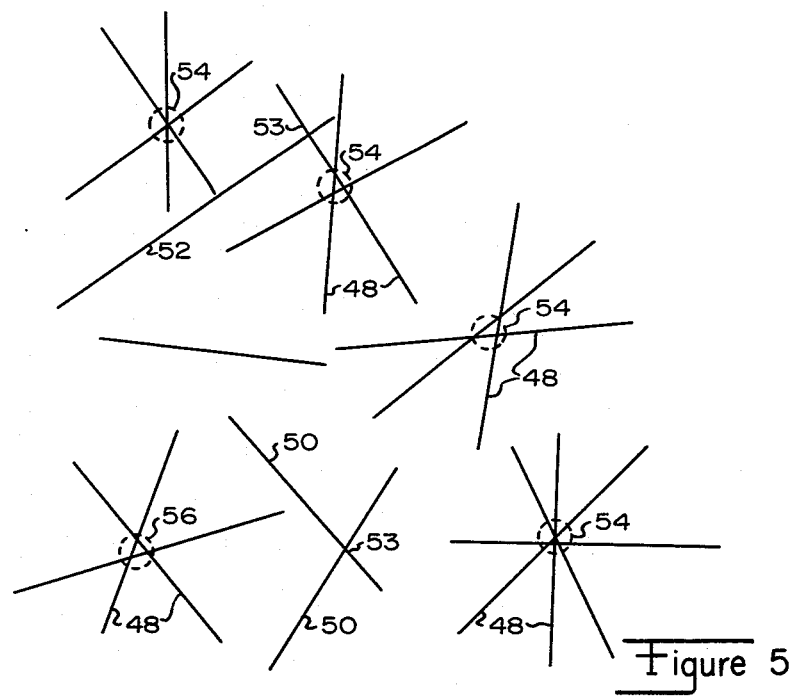
FIG. 5 is a pictorial representation of data accumulated during a single time bin of operation according to the present invention.

Subsequent computer processing of the stored data constructs straight lines in space corresponding to the inferred flight paths of the recorded gamma rays as represented in the pictorial presentation of FIG. 5. Three times out of four, at least one of the gamma rays will have been Compton scattered, producing a line 50 which does not pass through the point at which the gamma rays actually originated. These lines 50 are rejected in the data analysis because they do not consistently intersect other lines in the region of the same slowly-moving point in space. Intersections of the "true" lines will cluster together near one point 54 in space, corresponding to location of a source at a given time, which moves with a velocity of a few tens or hundreds of cm/sec. The intersections 53 of "spurious" lines are scattered randomly about and do not converge near any point.

It is desirable to minimize this background clutter of spurious lines against which the sources must be "seen", since the "true" lines do not pass through a perfect point of intersection, but through a region of ambiguity of a few millimeters in size, smeared by the variable distances and directions in which the positrons move from the source before annihilating and by the motion of the surface of the heart, where the coronary arteries of interest are located. In accordance with the present invention, the system can be operated through synchronized gates in order to observe sources only during the diastolic phase of the cardiac cycle when heart motion is least and the velocity of blood in the coronary arteries is greatest and most constant. Cardiac diastole characteristically occupies 400-600 milliseconds, which is considerably longer than the transit time (30-300 milliseconds) required for a particle to flow through a 10 cm length of coronary artery. As a result, data may be accumulated during a single diastolic period to provide a plurality of ray-intersection "clusters", as represented pictorially in FIG. 5.

Further computer processing of the intersections of the "true" straight lines reconstructs the positions of the positron-emitting sources in three dimensions as a function of time as they passed in the circulating blood through the field of view of the pairs of detector modules 7, 8 of FIG. 2. These intersections are accumulated in a number of time bins and are reconstructed to represent the flow paths of the particles. In practice, an operator may conveniently interface with the computer during this phase of data analysis to discriminate between the flow paths which represent transit through a coronary vessel and the flow paths which represent entrance to and exit from the chambers of the heart. This type of operator discrimination is simplified by the fact that these two kinds of flow paths are quite different, both spatially and with respect to relative flow velocities during the various phases of the cardiac cycle, and by the fact that an average of only three to four particles are typically in view at any one time.

In operation, then, an event is accepted by the hardwired electronics if a signal is received at two detector chambers within about 50 nanoseconds and if the spatial locations of the two chambers indicate the event originated in a small volume encompassing the heart. These events may be stored, for example, in a disc memory device.

Figure 6:
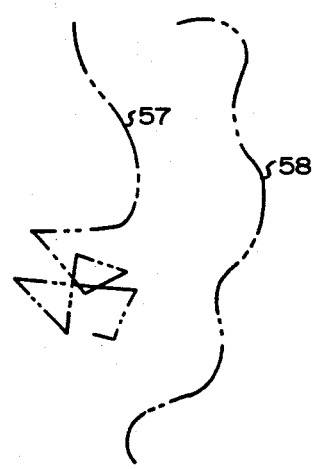
FIG. 6 is a pictorial representation of displayed data patterns representative of various particle trajectories in and about the heart of a subject.
Figure 4:
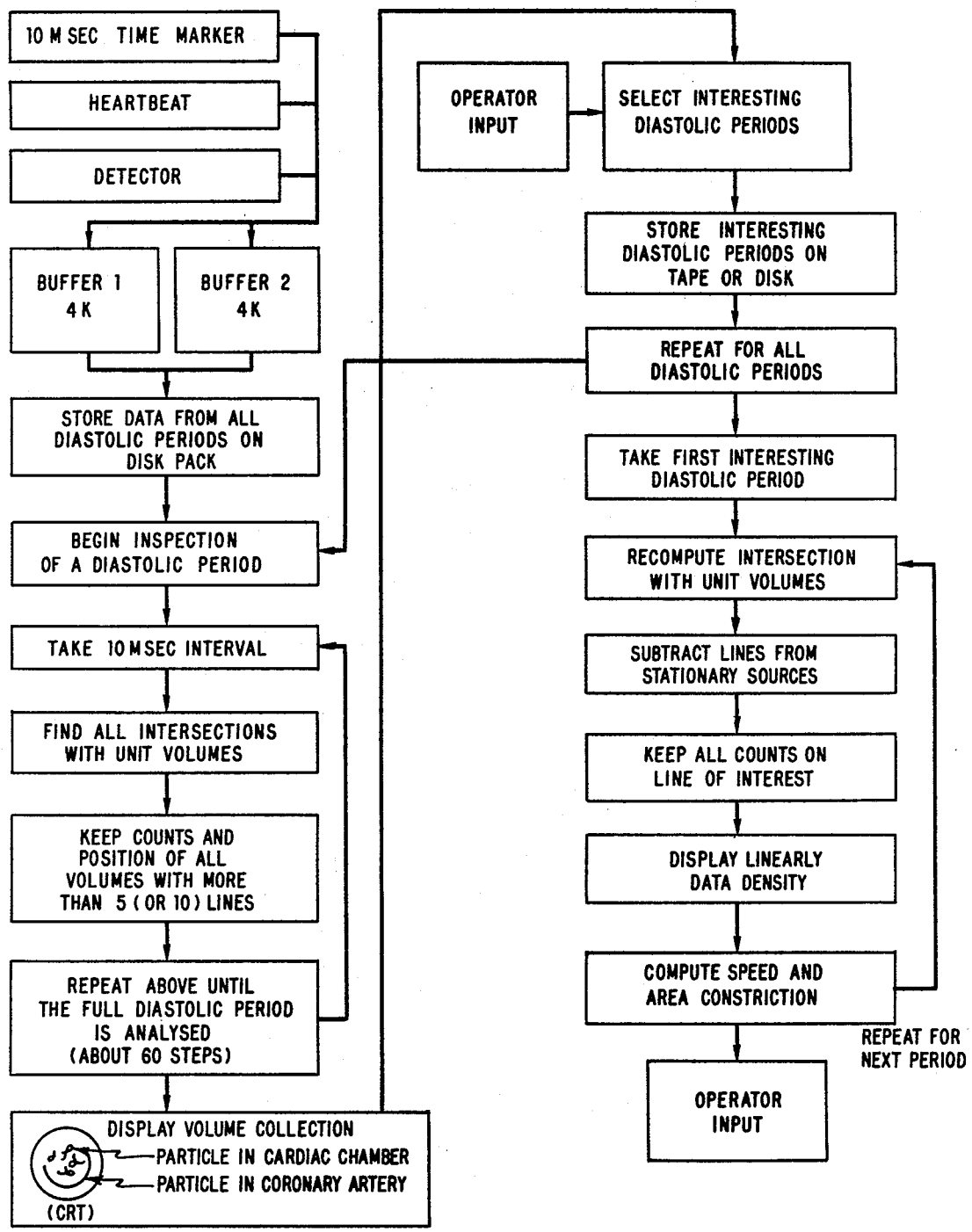
FIG. 4 is a process diagram showing operation of the data processor of FIG. 2.

The information thus stored may typically consist of 20 bits for the $x$, $y$ coordinates for each side of the detector, and 4 bits for gap identification within the module, if a multiple layer multi-wire proportional chamber is used as the detector. Thus, each event (a synchronous pair of gamma rays) may require four 12-bit words to identify it. In addition, ECG information and a 10 millisecond time marker may be stored on the disc to allow for correlation between the event and the cardiac cycle. Analysis may then be performed by the following steps:

Starting with the onset of cardiac diastole, the data can be divided into 10 millisecond time bins. Each bin may be analyzed on a 10 by 10 by 10 cm$^3$ matrix where the unit volume is 1 cubic cm. Each intersection of two or more lines (corresponding to the synchronous pair of gamma rays) within a unit volume is stored as an event and only those unit volumes with more than 5 (or 10) events stored in them will be selected. On the average, not more than two to five unit volumes will satisfy this criteria for each time bin. Storage may be provided for ten of them. The counts in the unit volume selected and its position may thus be stored separately and the process will be repeated for the next 10 millisecond period. Once all intervals within a diastolic period are analyzed, the intersections representative of the positions of the particles can be displayed sequentially, as shown pictorially in FIG. 6, for all time bins during a diastolic period. Particles that were resident in the cardiac chambers during diastole exhibit characteristic lines 57 having short random segments. Particles that flowed through a coronary vessel during diastole exhibit a long line 58 of characteristic contour corresponding to the course of a coronary artery. An operator may view these data patterns which represent transits of particles in and about the heart and perform simple data selection based upon the geometry of the flow transit paths 57, 58. Data corresponding to particles which passed through a coronary artery are selected and data corresponding to particles which entered into and resided in a cardiac chamber (or took some other extra-coronary path such as through a lung) are rejected.

The data thus selected for each path of interest during a diastolic period can be redisplayed on an effectively expanded time scale in order to determine the sequential location of each particle with greater time resolution. In stenotic regions of faster blood flow, a lower number of events per unit volume will be encountered and this information about sequential locations of a particle with respect to time is used to determine the relative velocities of a particle over the total course of the flow path along the coronary artery.

This process can be repeated for all diastolic periods of the examination and, from the information thus accumulated, the existence, location, severity and extent of stenotic and dilated regions of the coronary arteries can be determined.

THE PARTICLE RADIATORS

One important constraint governing the suitability of a positron source concerns the energy of the positrons emitted. It is desirable to limit the range that the positron travels in tissue before annihilation and conversion to gamma pairs in order to minimize the sphere of confusion in inferring the radionuclide position from intersection of the lines-of-flight of gamma pairs. Since the range of 1 MeV positron is about 0.5 gm/cm$^2$ or 5mm in tissue, it is desirable to have the mean positron energy below 1 MeV. The circulating particles should be no larger in their smallest diameter than 6–8 microns so that they will freely pass through capillary beds and each particle should produce at least $3 \times 10^5$ positrons per second. The specific activity (number of radioactive decays/second/gram) of a radionuclide required to furnish this positron rate in a particle of the small size indicated will depend upon the physiochemical properties of the radionuclide and the manner in which it forms particulates with carrier materials. The specific activity of a radionuclide is inversely proportional to its half-life. Acceptable half-lives must take into account the method of production of the radionuclide and the time required to chemically or physically convert the radionuclide into suitable particle form.

Gallium$_{68}$ is an attractive source candidate, because of its following radioactive properties:
 half-life: 68 minutes
 decay product: stable $^{68}$Zn
 modes of decay: 88%$^+$ of which 86% goes to ground state of $^{68}$Zn
 mean positron energy: 1 MeV
 production: from decay of Germanium$_{68}$, which has a half-life of 275 days Gallium$_{68}$ is a short-lived daughter continually produced by a long-lived parent. Germanium$_{68}$ "cows" are commercially available at low cost (less than $1,000 for the specific activity required for the worst case discussed above). The Gallium$_{68}$ produced by these generators is conveniently removed from the Germanium cow by eluting with an aqueous EDTA solution. Ga$_{68}$ can be liberated from the Ga-EDTA complex by mixing with a strongly acetic iron solution or boiling away the EDTA.

Gallium is a chemically highly reactive element which readily forms many inorganic, insoluble compounds with iron, tin, sulfates, chromates, phosphates, etc. One easily produced crystalline complex is (Ga)(Cr)(PO$_4$)$_2$, formed by adding a phosphate buffered chromic salt to the eluted Ga$_{68}$-EDTA complex and boiling away the EDTA and water. The resulting crystals may be conventionally pulverized and screened to the requisite size in a diluent suitable for intravascular administration. Of course, other radiation-emitting sources may be used in accordance with the present invention. For example, particulate X-ray sources may be introduced into the blood and the detection may be performed by recurring exposures for brief intervals of photographic film positioned about the thorax of a patient.

THE DETECTOR

The detector system consists of one or more pairs of modules 7, 8, 7', 8', preferably arranged surrounding the subject's chest, as shown in FIG. 2. Each module 7, 7', 8, 8' may be a sandwich of five multi-wire proportional chambers coupled to 1mm lead converters according to conventional design. Such modules have an active area of 50 cm × 50 cm and a total thickness of 5 cm. The 0.511 MeV annihilation photons are converted to electrons in the lead and the annihilation vectors are determined from two opposing multi-wire proportional chambers (FIG. 2). Detectors of this type, where multiplication without sparking is used to determine the position of events, are described in the literature (see, for example, Charpak, et al., Nucl. Inst. Methods 62:262, 1968; 65:217, 1968; 88:149, 1970). Detectors of this type may consist of three-wire grids with the central grid held at a positive d.c. voltage with respect to the outer two thirds. For the purpose of gamma ray imaging, one of the outer grids is replaced by a lead converter which is placed very close to the high voltage grid ($\approx 1$ mm). The two grids have wires at right angles to each other and can be placed further apart (5-10mm). The conversion electrons in passing through the gas in the chamber produce electron-ion pairs. These electrons are accelerated towards a positive high voltage wire, undergoing rapid multiplication in the high field region surrounding the wire. This results in a voltage pulse on the wire. A similar pulse is induced on the wires of the ground plane. Determining the wires on which these pulses occur gives the spatial location of the event. This may be done by capacitively coupling the wire grids to delay lines, as shown in FIG. 3. Measuring the time difference between the generation of the pulse and its arrival at the end of the delay line indicates the position of the origin of the pulse on the delay line and thus the spatial location of the event. The present technique allows spatial location accuracy of 1mm, data rates of over $10^5$/second and resolving times of the order of 30-60 nanoseconds. Of course, the wire grids may all be coupled to a central processing unit or computer for direct determination and location of simultaneously occurring pairs of annihilation photons.

Even for pure positron-emitting sources, the majority of detected events consists of a single gamma ray, the other escaping the system because of its limited acceptance and detection efficiency. Also, some of the annihilation photons may convert in tissues surrounding the source, thus further reducing potential coincidence counts in both detectors.

Considering only the hardware-related part of this problem and including a factor of 0.25 for Compton scatter of the annihilation photons, for identical detectors 7 and 8 mounted symmetrically on four sides of a cube as shown in FIG. 2, we may define:

G as the geometric acceptance of the system for the particular source position e as the efficiency for the detection of a single 511 KeV photon N as the number of annihilations per second occurring at the source $\tau$ as the resolving time of the chamber For the case of a pure positron emitter, we set:
$G = 0.66$
$e = 0.20$
$\tau = 50 \times 10^{-9}$ sec
$N = 10$ microcurie Ci $= 3.7 \times 10^5$ sec The rate of accidental coincidences A due to the detection of two uncorrelated events is:

$$A = G^2 e^2 N^2 \tau = 125/\text{sec}$$

which is distributed almost uniformly over the field, causing a low background data density. The number of real events R is:

$$R = 0.25 G e^2 N = 2.5 \times 10^3/\text{sec}$$

concentrated over a small volume. The singles average data rate at each chamber is:

$$S = G/2 \times e/5 \times N = 4.8 \times 10^3/\text{sec}$$

which is well within the capabilities of such a detector.

I claim:

1. Apparatus for interacting with a number of particles which can be introduced into the blood of a subject and which can provide signals from within a vessel of interest that can be detected outside the body, the apparatus comprising:
   detector means positionable near the body of the subject for detecting the signals from the number of particles at successive locations of each of the number of particles at successive times during the travel of each particle through a vessel of interest;
   circuit means coupled to said detector means for providing output manifestations from successive positions of each of the number of particles at successive times during the travel thereof through the vessel of interest; and
   output means responsive to the output manifestations from said circuit means for providing an indication of the relative internal cross-sectional areas of the vessel of interest at successive positions along the cource of the vessel of interest.

2. Apparatus according to claim 1 for interaction with a number of particles which can produce radiation that passes through the body walls of the subject; and wherein:
   said detector means is positionable near the body of the subject for receiving the radiation emanating from the body of the subject to produce electrical signals in response thereto.

3. Apparatus as in claim 2 wherein said circuit means includes gate means and coincidence means connected thereto for controlling the transmission therethrough of only electrical signals from said detector means which are indicative of substantially oppositely propagating gamma rays that are received from the body of the subject within a selected time interval of separation between occurrences.

4. Apparatus as in claim 3 wherein said coincidence means controls said gate means to transmit therethrough only the electrical signals produced by said detector means within a time interval of not greater than 50 nanoseconds.

5. Apparatus as in claim 3 wherein said circuit means includes gate means and coincidence means connected thereto for controlling the transmission therethrough of only coincident electrical signals produced by said detector means in response to oppositely-directed pairs of gamma rays received thereby along a straight line which may intersect a vessel of interest in the body of a subject about which the detector means is positioned.

6. Apparatus as in claim 2 wherein said detector means produces electrical signals in response to gamma rays received thereby of energies of approximately 0.5 MeV.

7. Apparatus as in claim 2 wherein said detector means has a resolution of at least about 5 millimeters.

8. Apparatus as in claim 2 wherein said circuit means includes input means connected to receive electrocardiographic signals from the subject for controlling said circuit means to selectively respond to said electrical signals from the detector means during a selected portion of the cardiac cycle of the subject.

9. Apparatus as in claim 8 wherein said circuit means includes coincidence means and timing means connected to control said circuit means for producing data signals representative of the occurrence and locations of pairs of electrical signals produced by said detector means during each of a plurality of time intervals determined by said timing means and occurring as determined by said coincidence means in substantial coincidence within said diastolic portion of the cardiac cycle of the subject.

10. Apparatus as in claim 1 wherein said circuit means includes timer means for providing said output manifestations from each of said particles in the vessel of interest at successive times occurring at approximately 1 to 10 millisecond intervals.

11. Apparatus as in claim 1 wherein said detector means is capable of being positioned to within approximately two-thirds solid angle around the heart of said subject.

12. Apparatus as in claim 1 wherein said circuit means includes data storage means for recording said output manifestations of each of the number of particles as a function of time.

13. Apparatus according to claim 1 for interaction with a number of particles which produce gamma rays that pass through the body walls of the subject, and wherein said detector means is positionable near the body of the subject for receiving gamma rays emanating from the body of the subject to produce electrical signals in response thereto.

14. Apparatus according to claim 13 wherein said detector means includes portions which are positionable near the body of the subject for receiving gamma rays emanating in substantially opposite directions from the subject to produce electrical signals in response thereto.

15. Apparatus for interacting with a number of particles which can be introduced into the blood of a subject and which can produce radiation from within a vessel of interest that passes through the body walls of the subject in substantially opposite directions from the location of the particle within the body, the apparatus comprising:

detector means positionable about the body of the subject for receiving the radiation emanating in substantially opposite directions from the body of the subject to produce electrical signals in response thereto which are indicative of successive locations of each of the number of particles at successive times during travel of each particle through the vessel of interest; and circuit means including timing means coupled to said detector means for providing output manifestations indicative of the three-dimensional coordinates of successive positions of each of the number of particles which is within the vessel of interest and from which the detector means receives oppositely-directed radiation in substantial coincidence during a time interval determined by said timing means, said circuit means including signal selecting means connected to receive said output manifestations for producing an output therefrom in response to the occurrence of at least three pairs of coordinates represented by said output manifestations for a selected time interval attaining values which correspond to at least three straight lines connecting such pairs of coordinates substantially intersecting at a location within the vessel of interest, thereby to identify the location of a positron-emitting particle in the vessel of interest, and outut means responsive to the outputs from said signal selecting means for providing an indication of successive positions of a particle along the course of a vessel of interest.

16. Apparatus as in claim 15 wherein said circuit means includes display apparatus responsive to the outputs from said signal selecting means for providing an output indication of sequential locations as a function of time of said intersections to provide an indication of the relative internal cross-sectional areas of the vessel of interest at successive positions along the course of the vessel of interest.

17. Apparatus as in claim 15 wherein said circuit means includes data processing means responsive to the successive locations during each of said time intervals of said intersections representing a particle for indicating the relative cross-sectional areas at various locations along a vessel of interest, thereby to determine the existence, severity and location of stenotic or dilated regions of said blood vessel.

18. Apparatus as in claim 15 wherein said circuit means includes display apparatus responsive to the outputs from said signal selecting means for providing an output indication of sequential locations as a function of time of said intersections to provide an indication of the course of the vessel of interest.

19. Apparatus as in claim 15 wherein said circuit means includes data processing means responsive to the successive locations during each of said time intervals of said intersections representing a particle for indicating the course of the vessel of interest.

20. The method for determining the existence, location and severity of stenosis or dilations of regions of selected blood vessels within the body of a subject, the method comprising the steps of:

introducing into the blood of the subject a number of particulate sources of radiation which can produce radiation from within a vessel of interest that can pass through the body walls of the subject;

detecting the radiation emanating from the body of the subject to determine the successive locations of the radiation source and the relative frequency of occurrence of the detected radiation;

determining therefrom the course of the vessel of interest within the body of the subject and the relative frequency of occurrence of detected radiation per unit length along the course of the vessel of interest; and ascertaining therefrom the relative internal cross-sectional areas of the vessel of interest from the direct relationship thereof to the frequency of occurrences of detected radiation per unit length of the vessel of interest.

21. The method as in claim 20 wherein in the step of introducing particulate sources, introducing particulate sources of positrons having energy levels not higher than approximately 1 MeV.

22. In the method according to claim 20, the additional steps of detecting the electrocardiographic signals from the subject to identify therefrom the diastolic portion of the cardiac cycle of the subject, and limiting the step of detecting the radiation emanating from the body of the subject only during said diastolic portion of the cardiac cycle.

23. The method according to claim 20 wherein in the step of introducing particulate sources of radiation, the particulate sources are introduced by peripheral venous injection to pass through the capillary beds of the body of the subject to be detected in an artery of interest.

24. The method according to claim 20 wherein in the step of detecting radiation, detecting gamma rays.

25. The method as in claim 24 wherein in the step of detecting, detecting only pairs of gamma rays received from the body of the subject in substantial coincidence from substantially opposite directions with respect to the selected vessel to produce said signals indicative of said locations.

26. The method as in claim 25 wherein in the step of detecting, selecting pairs of substantially coincident, oppositely-directed gamma rays which have coordinates for each pair that correspond to the substantial intersection of three straight lines connecting said coordinate pairs, each of these intersections occurring at a location within a vessel of interest to identify the successive locations of a positron-emitting particle flowing therewithin.

27. The method as in claim 26 including the step of accumulating the number of pairs of substantially coincident, oppositely-directed gamma rays whose coordinates are associated with said intersections occurring during successive time periods.

28. The method as in claim 27 including the step of displaying the successive locations of the flowing positron-emitting particles to select therefrom a particular vessel for analysis of the relative frequency of occurrence of said accumulated numbers of pairs per unit length of the particular vessel.

29. The method as in claim 28 comprising the additional step of analyzing the relative frequency of occurrence of said accumulated numbers of pairs per unit length of said particular vessel to indicate in direct relationship thereto the relative internal cross-sectional areas along the length of said particular vessel.

30. Apparatus for interacting with a number of particles which can be introduced into the blood of a subject and which can provide signals from within a vessel of interest that can be detected outside the body, the apparatus comprising:
   detector means positionable near the body of the subject for receiving the signals emanating from the body of the subject to produce electrical signals in response thereto which are indicative of the successive locations of a particle from which the received signals emanated from the body;
   circuit means responsive to said electrical signals for providing output manifestations indicative of the three-dimensional coordinates of successive locations of each of said particles within said vessel of interest as a function of time; and
   output means responsive to the output manifestations from said circuit means for providing an indication of the course of the vessel.

31. Apparatus according to claim 30 for interaction with a number of particles which can produce radiation that passes through the body walls of the subject; and wherein:
   said detector means is positionable near the body of the subject for receiving the radiation emanating from the body of the subject to produce electrical signals in response thereto.

32. Apparatus as in claim 31 wherein said circuit means includes gate means and coincidence means connected thereto for controlling the transmission therethrough of only electrical signals from said detector means which are indicative of substantially oppositely propagating gamma rays that are received from the body of the subject within a selected time interval of separation between occurrences.

33. Apparatus as in claim 32 wherein said coincidence means controls said gate means to transmit therethrough only the electrical signals produced by said detector means within a time interval of not greater than 50 nanoseconds.

34. Apparatus as in claim 32 wherein said circuit means includes gate means and coincidence means connected thereto for controlling the transmission therethrough of only coincident electrical signals produced by said detector means in response to oppositely-directed pairs of gamma rays received thereby along a straight line which may intersect a vessel of interest in the body of a subject about which the detector means is positioned.

35. Apparatus as in claim 31 wherein said detector means produces electrical signals in response to gamma rays received thereby of approximately 0.5 MeV.

36. Apparatus as in claim 31 wherein said detector means has a resolution of at least about 5 millimeters.

37. Apparatus as in claim 30 wherein said circuit means includes timer means for providing said output manifestations from each of said particles in the vessel of interest at successive times occurring at approximately 1 to 10 millisecond intervals.

38. Apparatus as in claim 30 wherein said detector means is positioned to within approximately two-thirds solid angle around the body of the subject.

39. Apparatus as in claim 30 wherein said circuit means includes data storage means for recording said output manifestations of each of the number of particles as a function of time.

40. Apparatus as in claim 30 wherein said circuit means includes input means connected to receive electrocardiographic signals from the subject for controlling said circuit means to selectively respond to said electrical signals from the detector means during a selected portion of the cardiac cycle of the subject.

41. Apparatus as in claim 40 wherein said circuit means includes coincidence means and timing means connected to control said circuit means for producing data signals representative of the occurrence and locations of pairs of electrical signals produced by said detector means during each of a plurality of time intervals determined by said timing means and occurring as determined by said coincidence means in substantial coincidence within said diastolic portion of the cardiac cycle of the subject.

42. Apparatus according to claim 30 for interaction with a number of particles which can produce gamma rays that pass through the body walls of the subject; and wherein said detector means is positionable near the body of the subject for receiving gamma rays emanating from the body of the subject to produce electrical signals in response thereto.

43. Apparatus according to claim 42 wherein said detector means includes portions which are positionable near the body of the subject for receiving gamma rays emanating in substantially opposite directions from the subject to produce electrical signals in response thereto.

44. The method of determining the course of a blood vessel of interest within the body of a subject, the method comprising the steps of:
introducing into the blood stream of the subject one or more particles capable of providing signals detectable from outside the body to flow with the blood through the blood vessel of interest;
establishing a field of detection which encompasses the blood vessel of interest and tracking through the field of detection the successive locations of each particle as it flows through the blood vessel of interest; and
determining therefrom the course of the vessel of interest.

45. The method according to claim 44 wherein in the step of introducing, the particles are introduced by peripheral venous injection to pass through the capillary bed of the body of the subject to be detected in an artery of interest.

46. The method according to claim 44 wherein in the step of introducing, particulate sources of radiation which can produce radiation that can pass through the body walls of the subject are introduced into the blood stream, and comprising the step of detecting radiation.

47. The method as in claim 46 wherein in the step of detecting, detecting only pairs of gamma rays received from the body of the subject in substantial coincidence from substantially opposite directions with respect to the selected vessel to produce said signals indicative of said locations.

48. The method for determining the course of a blood vessel of interest within the body of a subject, the method comprising the steps of:
introducing into the blood of the subject a number of particulate sources of radiation which can produce radiation from within a vessel of interest that can pass through the body walls of the subject;
detecting the electrocardiographic signals from the subject to identify therefrom the diastolic portion of the cardiac cycle of the subject;
detecting the radiation emanating from the body of the subject only during said diastolic portion of the cardiac cycle to determine the three-dimensional coordinates of successive locations of the radiation source; and
determining therefrom the course of the vessel of interest within the body of the subject.

49. The method for determining the course of a blood vessel of interest within the body of a subject, the method comprising the steps of:
introducing into the blood of the subject a number of particulate sources of radiation which can produce gamma rays from within a vessel of interest that can pass through the body walls of the subject;
detecting only pairs of gamma rays received from the body of the subject in substantial coincidence from substantially opposite directions with respect to the vessel of interest;
selecting pairs of substantially coincident, oppositely-directed gamma rays which have coordinates for each pair that correspond to the substantial intersection of three straight lines connecting said coordinate pairs, each of these intersections occurring at a location within a vessel of interest to identify the successive locations of a particulate source flowing therewithin; and
determining therefrom the course of the vessel of interest within the body of the subject.

50. The method according to claim 49 including the step of accumulating the number of pairs of substantially coincident, oppositely-directed gamma rays whose coordinates are associated with said intersections occurring during successive time periods.

51. The method as in claim 50 including the step of displaying the successive locations of the flowing positron-emitting particles to indicate therefrom the course of the vessel of interest.

* * * * *